US008003361B2

(12) United States Patent  
Brady et al.

(10) Patent No.: US 8,003,361 B2  
(45) Date of Patent: Aug. 23, 2011

(54) PRODUCTION OF MONATIN ENANTIOMERS

(75) Inventors: Dean Brady, Midrand (ZA); Lucia H. Steenkamp, Boksburg (ZA); Amanda Louise Rousseau, Bedford Gardens (ZA); Subash Buddoo, Randburg (ZA); Paul A. Steenkamp, Boksburg (ZA)

(73) Assignee: Cargill Incorporated, Wayzata, MN (US)

( * ) Notice: Subject to any disclaimer, the term of this patent is extended or adjusted under 35 U.S.C. 154(b) by 386 days.

(21) Appl. No.: 11/865,403

(22) Filed: Oct. 1, 2007

(65) Prior Publication Data

US 2009/0087829 A1    Apr. 2, 2009

(51) Int. Cl.
*C12N 9/18* (2006.01)
*C12Q 1/00* (2006.01)
*C12P 17/16* (2006.01)
*C12P 17/10* (2006.01)
*C07D 209/20* (2006.01)
*C07D 209/12* (2006.01)

(52) U.S. Cl. ............ 435/197; 435/4; 435/118; 435/121; 548/497; 548/494; 548/240

(58) Field of Classification Search .................. None
See application file for complete search history.

(56) References Cited

U.S. PATENT DOCUMENTS

| | | | |
|---|---|---|---|
| 3,002,889 A | 10/1961 | Kinoshita et al. |
| 3,751,458 A | 8/1973 | Wiley |
| 3,936,472 A | 2/1976 | Kinney et al. |
| 4,010,204 A | 3/1977 | Koster et al. |
| 4,975,298 A | 12/1990 | Van Wyk et al. |
| 5,128,164 A | 7/1992 | Van Wyk et al. |
| 5,128,482 A | 7/1992 | Olivier et al. |
| 5,545,644 A | 8/1996 | Macor et al. |
| 5,703,270 A | 12/1997 | Nakagawa et al. |
| 5,994,559 A | 11/1999 | Abushanab et al. |
| 6,218,167 B1 | 4/2001 | Allen et al. |
| 6,264,999 B1 | 7/2001 | Yatka et al. |
| 6,277,626 B1 | 8/2001 | Hansen et al. |
| 6,489,100 B1 | 12/2002 | Liao |
| 6,743,910 B2 | 6/2004 | Cimpoia et al. |
| 7,064,219 B2 | 6/2006 | Kawahara et al. |
| 7,081,359 B2 | 7/2006 | Lim |
| 7,354,746 B1 | 4/2008 | Suzuki et al. |
| 7,396,941 B2 | 7/2008 | Mori et al. |
| 7,534,898 B2 | 5/2009 | Amino et al. |
| 7,781,005 B2 | 8/2010 | Mori |
| 7,816,541 B2 | 10/2010 | Kawahara et al. |
| 7,888,081 B2 | 2/2011 | Khare et al. |
| 2003/0228403 A1 | 12/2003 | Amino et al. |
| 2004/0063175 A1 | 4/2004 | Abraham et al. |
| 2005/0004394 A1 | 1/2005 | Kawahara et al. |
| 2005/0009153 A1 | 1/2005 | Sugiyama et al. |
| 2005/0020508 A1 | 1/2005 | Amino et al. |
| 2005/0106305 A1 | 5/2005 | Abraham et al. |
| 2005/0112260 A1 | 5/2005 | Abraham et al. |
| 2005/0118317 A1 | 6/2005 | Amino et al. |
| 2005/0137246 A1 | 6/2005 | Amino et al. |
| 2005/0153405 A1 | 7/2005 | Sugiyama et al. |
| 2005/0170041 A1 | 8/2005 | Abraham et al. |
| 2005/0221453 A1 | 10/2005 | Takagi et al. |
| 2005/0221455 A1 | 10/2005 | McFarlan et al. |
| 2005/0244937 A1 | 11/2005 | Abraham et al. |
| 2005/0244939 A1 | 11/2005 | Sugiyama et al. |
| 2005/0272939 A1 | 12/2005 | Amino et al. |
| 2005/0282260 A1 | 12/2005 | Hicks et al. |
| 2006/0003411 A1 | 1/2006 | Sugiyama et al. |
| 2006/0003426 A1 | 1/2006 | Sugiyama et al. |
| 2006/0009394 A1 | 1/2006 | Amino |
| 2006/0014819 A1 | 1/2006 | Mori et al. |
| 2006/0074249 A1 | 4/2006 | Kawahara et al. |
| 2006/0083695 A1 | 4/2006 | Mori |
| 2006/0154343 A1 | 7/2006 | Mori et al. |
| 2006/0172396 A1 | 8/2006 | Sugiyama et al. |
| 2006/0252135 A1 | 11/2006 | Brazeau et al. |
| 2007/0099277 A1 | 5/2007 | Anderson et al. |
| 2007/0105938 A1 | 5/2007 | Anderson et al. |
| 2008/0020434 A1 | 1/2008 | Brazeau et al. |
| 2008/0020435 A1 | 1/2008 | Burke et al. |
| 2008/0274518 A1 | 11/2008 | Hicks et al. |
| 2009/0087888 A1 | 4/2009 | Buddoo et al. |
| 2009/0088577 A1 | 4/2009 | Buddoo et al. |
| 2009/0117625 A1 | 5/2009 | Abraham et al. |
| 2009/0130285 A1 | 5/2009 | Abraham et al. |
| 2009/0198072 A1 | 8/2009 | Khare et al. |
| 2010/0221795 A1 | 9/2010 | Takakura et al. |
| 2011/0020882 A1 | 1/2011 | de Souza et al. |
| 2011/0045547 A1 | 2/2011 | de Souza et al. |

FOREIGN PATENT DOCUMENTS

EP          0 438 314          4/1994

(Continued)

OTHER PUBLICATIONS

Fuganti et al. Kinetic resolution of substituted 2,3-4H-5,6-dihydrooxazines with carboxylesterase NP: synthesis of (3S, 1'R)-3-(1'-hydroxyethyl)-azetidine-2-one, Bioorganic & Medicinal Chemistry, 2(7):723-726, 1994.*
Chica et al. Semi-rational Approaches to engineering enzyme activity: combining the benefits of direcred evolution and rational design, Curr Opin Biotechnol. Aug. 2005; 16(4):378-84. Review.*
Buldain et al., "Carbon-13 Nuclear Magnetic Resnoance Spectra of the Hydrate, Keto, and Enol Forms of Oxalacetic Acid," *Magnetic Resonance Chemistry*, 1985, 23(6):478-481.
Guo et al., "Protein tolerance to random amino acid charge," *Proc. Natl. Acad. Sci. USA*, 2004, 101(25):9205-9210.
Seffernick et al., "Melamine deaminase and atrazine chlorohydrolase: 98 percent identical but functionally different," *J. Bacteriology*, 2001, 183(8):2405-2410.
Seo Jeong-Sun et al., "The genome sequence of the ethanologenic bacterium *Zymomonas mobilis* ZM4," *Nature Biotechnology*, 2005, 23(1):63-68.

(Continued)

*Primary Examiner* — Anand Desai
*Assistant Examiner* — Iqbal H Chowdhury

(57) ABSTRACT

Methods for preferentially hydrolyzing one stereoisomer of an isoxazoline diester over another, as well as an enzyme for facilitating the preferential hydrolysis are provided. Also provided are methods for providing mixtures of (RR) and (RS) monatin as well as (SS) and (SR) monatin, which methods can include the step of stereoselectively hydrolyzing an isoxazoline diester.

15 Claims, 2 Drawing Sheets

FOREIGN PATENT DOCUMENTS

| | | |
|---|---|---|
| EP | 1 045 029 | 10/2000 |
| EP | 1 350 791 | 10/2003 |
| EP | 1 445 323 | 8/2004 |
| EP | 1 449 832 | 8/2004 |
| EP | 1 533 376 | 5/2005 |
| EP | 1 580 268 | 9/2005 |
| EP | 1 605 041 | 12/2005 |
| EP | 1 719 758 | 11/2006 |
| JP | 2002-060382 | 2/2002 |
| JP | 2003-171365 | 6/2003 |
| JP | 2004-222657 | 8/2004 |
| JP | 2004-331644 | 11/2004 |
| JP | 2004-331650 | 11/2004 |
| WO | WO 89/11212 | 11/1989 |
| WO | WO 03/045914 | 6/2003 |
| WO | WO 03/056026 | 7/2003 |
| WO | WO 03/059865 | 7/2003 |
| WO | WO 03/091396 | 11/2003 |
| WO | WO 2005/001105 | 1/2005 |
| WO | WO 2005/014839 | 2/2005 |
| WO | WO 2005/016022 | 2/2005 |
| WO | WO 2005/020721 | 3/2005 |
| WO | WO 2005/042756 | 5/2005 |
| WO | WO 2005/082850 | 9/2005 |
| WO | WO 2006/011613 | 2/2006 |
| WO | WO 2006/113897 | 10/2006 |
| WO | WO 2006/116487 | 11/2006 |
| WO | WO 2007/103389 | 9/2007 |
| WO | WO 2007/133183 | 11/2007 |
| WO | WO 2007/133184 | 11/2007 |
| WO | WO2010/105014 | 9/2010 |
| WO | WO2010-138513 | 12/2010 |

OTHER PUBLICATIONS

Whisstock et al., "Prediction of protein function from protein sequence," *Q. Rev. Biophysics*, 2003, 36(3):307-340.

Witkowski et al., "Conversion of b-ketoacyl synthase to a malonyl decarboxylase by replacement of the active-site cysteine with glutamine," *Biochemistry*, 1999, 38:11643-11650.

Ackerman, "Structure elucidation of and synthetic approaches to monatin, a metabolite from schlerochiton ilicifolius," PhD dissertation, University of Stellenbosch, Jul. 1990.

Ager et al., "Commercial, Synthetic Nonnutritive Sweeteners," *Agnew. Chem. Int. Ed.*, 1998, 37:1802-1817.

Ager et al., "Novel biosynthetic routes to non-proteinogenic amino acids as chiral pharmaceutical intermediates," *Journal of Molecular Catalysis B: Enzymatic*, 2001, 11:199-205.

Azuma et al., "Hyper-production of L-tryptophan via fermentation with crystallization," *Appl. Microbiol. Biotechnol.*, 1993, 39:471-476.

Bae et al., "Production of aromatic D-amino acids from α-keto acids and ammonia by coupling of four enzyme reactions," *Journal of Molecular Catalysis B: Enzymatic*, 1999, 6:241-247.

Bassoli, "'Chemistry-Nature,' still an open match for the discovery of new intensive sweeteners," *Agro FOOD industry hi-tech*, 2004, 15(4):27-29.

Bassoli et al., "Design and synthesis of new monatin derivatives," *Abstracts, 13th International Symposium on Olfaction and Taste (ISOT XIII), 14th. European Chemoreception Research Organization Congress (ECRO XIV)*, Jul. 20-24, 2000, p. 162.

Bassoli et al., "General Pseudoreceptor Model for Sweet Compounds: A Semiquantitative Prediction of Binding Affinity for Sweet-Tasting Molecules," *J. Med. Chem.*, 2002, 45:4402-4409.

Bassoli et al., "Monatin and Its Stereoisomers: Chemoenzymatic Synthesis and Taste Properties," *Eur. J. Org. Chem.*, 2005, 8:1652-1658.

Bhatnagar et al., "The Broad-specificity, Membrane-bound Lactate Dehydrogenase of *Neisseria gonorrhoeae*: Ties to Aromatic Metabolism," *J. Gen. Microbiol.*, 1989, 135:353-360.

Bommarius et al., "Some new developments in reductive amination with cofactor regeneration," *Biocatalysis*, 1994, 10:37-47.

Bongaerts et al., "Metabolic Engineering for Microbial Production of Aromatic Amino Acids and Derived Compounds," *Metabolic Engineering*, 2001, 3:289-300.

Brandl and Lindow, "Cloning and characterization of a locus encoding an indolepyruvate decarboxylase involved in indole-3-acetic acid synthesis in *Erwinia herbicola*," *Appl. Environ. Microbiol.*, 1996, 62:4121-4128.

Camargo, "Preparation of amino acids not proteinogênicos, structurally related to adoçante natural Monatina" [translated by Google], Jan. 2003, Universidade Estadual de Campinas Instituto de Quimica, Dissertation of Masters.

Curran, "Reduction of .DELTA.2-isoxazolines: a conceptually different approach to the formation of aldol adducts," *J. Am. Chem. Soc.*, 1982, 104:4024-4026.

DeLuna et al., "NADP-Glutamate Dehydrogenase Isoenzymes of *Saccharomyces cerevisiae*: Purification, Kinetic Properties, and Physiological Roles," *J. Biol. Chem.*, 2001, 276(47):43775-43783.

Floyd et al., "A Simple Strategy for obtaining both Enantiomers from an Aldolase Reaction: Preparation of L- and D-4-Hydroxy-2-ketoglutarate," *J. Chem. Soc. Perkin Trans. 1*, 1992, 1085-1086.

Henderson et al., "Stereospecific Preparation of the N-Terminal Amino Acid Moiety of Nikkomycins KX and KZ via a Multiple Enzyme Synthesis," *J. Org. Chem.*, 1997, 62:7910-7911.

Holzapfel et al., "A simple cycloaddition approach to a racemase of the natural sweetener monatin," *Synthetic Communications*, 1994, 24(22):3197-3211.

Holzapfel et al., "The synthesis of a gamma-keto-alpha-amino acid, a key intermediate in the synthesis of monatin, a new natural sweetner," *Synthetic Communications*, 1993, 23(18):2511-2526.

Izumi, "Introduction," Synthetic Production and Utilization of Amino Acids, 1974, Kankeko et al. (eds.), Halstad Press, Chapter 1, pp. 3-16.

Juhl et al., "Catalytic asymmetric homo-aldol reaction of pyruvate—a chiral Lewis acid catalyst that mimics aldolase enzymes," *Chem. Commun.*, 2000, 2211-2212.

Kogiso et al., "Control of Lactamization during the Synthesis of the Monatin Analogue," *Peptide Science*, 2003, pp. 195-198.

Kogiso et al., "The C-C Bond Formation with Alkyl Halide in Monatin Analogue Synthesis and Their Tastes Expression," *Peptide Science*, 2004, Shimohigashi (ed.), Japanese Peptide Society, pp. 165-168.

Li et al., "Nonproteinogenic alpha-Amino Acid Preparation Using Equilibrium Shifted Transamination," *Organic Process Research & Development*, 2002, 6:533-538.

Nakamura et al., "Total Synthesis of Monatin," *Organic Letters*, 2000, 2(19):2967-2970.

Nakamura et al., "Total Synthesis of Monatin and the Taste Experience," *Peptide Science*, 2003, pp. 61-64

Oliveira et al., "Highly diastereoselective alkylation of a pyroglutamate derivative with an electrophile obtained from indole. Synthesis of a potential intermediate for the preparation of the natural sweetener (−)-monatin," *Synthetic Communications*, 2000, 30(12):2143-2159.

Oliveira et al., "Diastereoselective formation of a quaternary center in a pyroglutamate derivative. Formal sythensis of Monatin," *Tetrahedron Letters*, 2001,42:6793-6796.

Tamura et al., "Highly stereoselective synthesis of (−)-monatin, a high-intensity sweetener, using chelation-controlled nitrone cycloaddition," *Chemical Communications*, 2003, 21:2678-2679.

Tamura et al., "Stereoselective Synthesis of 4-Hydroxy 4-Substituted Glutamic Acids," *J. Org. Chem.*, 2005, 70(12):4569-77.

Vleggaar et al., "Structure elucidation of monatin, a high-intensity sweetener isolated from the plant *Schlerochiton ilicifolius*," *J. Chem.*

*Soc. Perkin Transactions 1: Organic and Bio-Organic Chemistry.* (1972-1999), 1992, 22:3095-3098.

Curran et al., "Reduction of .DELTA.2-isoxazollnes. 3. Raney nickel catalyzed formation of .beta.-hydroxy ketones," J. Am, Chem. Soc., 1983. 105:5826-5833.

Gosset et al., "A direct comparison of approaches for increasing carbon flow to arornaflc biosynthesis in *Escherichia coli*" J of Ind Microbiology, 1996, 17:47-52.

Moriya et al, "A facile synthesis of 6-chloro-D-tryptophan", Bulletin of the Chemical Society of Japan, 1975, vol. 48,: 2217-2218 (abstract).

Wolf at al., "A Biocatalytic Route to Enaritiomerically Pure Unsaturated -H—Amino Adds," Adv. Sypth. & Catalysis, 2001, 343:662-674.

* cited by examiner

PRODUCTION OF MONATIN ENANTIOMERS

FIELD OF THE INVENTION

The present invention is in the field of organic and biocatalytic synthesis.

BACKGROUND

Monatin is a high-intensity sweetener having the chemical formula:

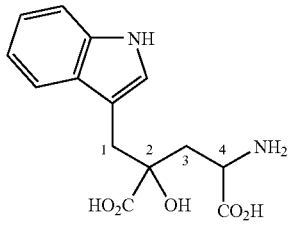

Because of various naming conventions, monatin is also known by a number of alternative chemical names, including: 2-hydroxy-2-(indol-3-ylmethyl)-4-aminoglutaric acid; 4-amino-2-hydroxy-2-(1H-indol-3-ylmethyl)-pentanedioic acid; 4-hydroxy-4-(3-indolylmethyl)glutamic acid; and, 3-(1-amino-1,3-dicarboxy-3-hydroxy-but-4-yl)indole.

Monatin contains two chiral centers leading to four potential stereoisomeric configurations. The R,R configuration (the "R,R stereoisomer" or "(R,R)-monatin"); the S,S configuration (the "S,S, stereoisomer" or "(S,S,)-monatin"); the R,S configuration (the "R,S stereoisomer" or "(R,S)-monatin"); and the S,R configuration (the "S,R stereoisomer" or "(S,R)-monatin"). The different stereoisomers of monatin have different sweetening characteristics. For example, (S,S)-monatin is approximately 50-200 times sweeter than sucrose by weight, while (R,R)-monatin is approximately 2000-2400 times sweeter than sucrose by weight.

Certain isomeric forms of monatin can be found in the bark of roots of the *Schlerochiton ilicifolius* plant located predominantly in the Limpopo region, but also in Mpumalanga and the North West Province of South Africa. However, the concentration of the monatin present in the dried bark, expressed as the indole in its acid form, has been found to be about 0.007% by mass. See U.S. Pat. No. 4,975,298. The exact method by which monatin is produced in the plant is presently unknown.

At least in part because of its sweetening characteristic and utility in food applications (including beverages), it is desirable to have an economic source of monatin. Furthermore, because of the different sweetening characteristics of the different stereoisomers, it is desirable to have an economic source of a single stereoisomer of monatin, such as the R,R stereoisomer. Thus, there is a continuing need to develop methods for the production of monatin in stereoisomerically-pure or stereoisomerically-enriched form.

SUMMARY

The invention provides methods for the production of the high intensity sweetener monatin from an enantiomerically-pure or enantiomerically-enriched isoxazoline ester.

In some embodiments of the invention, an isoxazoline diester undergoes enantioselective hydrolysis to produce enantiomerically-pure or enantiomerically-enriched isoxazoline monoester and enantiomerically-pure or enantiomerically-enriched isoxazoline diester. In some embodiments, the enantioselective hydrolysis preferentially acts on the isoxazoline diester "R"-isomer over the isoxazoline diester "S"-isomer resulting in enantiomerically-pure or enantiomerically-enriched R-isoxazoline monoester and enantiomerically-pure or enantiomerically-enriched S-isoxazoline diester. The monoester and diester can then be separated, and once separated each can then be converted to its corresponding monatin isomers. Thus, for example, where the enzyme is stereospecifically active for R-isoxazoline diester, a mixture of the R,R and R,S forms of monatin can be produced from the R-isoxazoline monester and a mixture of the S,S and S,R forms of monatin can be produced from the S-isoxazoline diester. In some embodiments, the resultant R,R and R,S forms of monatin are separated from one another, for example by physical means known in the art. In some embodiments the resultant S,S and S,R forms of monatin are separated from one another, for example by physical means known in the art.

In some embodiments of the invention, methods of identifying enzymes useful for producing stereoisomerically-pure or stereoisomerically-enriched monatin compositions is provided. In some embodiments, the method comprises screening hydrolytic enzymes for stereoselective hydrolytic activity on an isoxazoline diester. The screening comprises selecting a hydrolytic enzyme, such as hydrolases, including microbial lipases and esterases, forming a reaction mixture comprising the selected enzyme and an isoxazoline diester, providing conditions under which a hydrolysis reaction of the isoxazoline diester would be expected to occur, and analyzing the reaction mixture for the presence of isoxazoline monoester in enantiomerically-pure or enantiomerically-enriched form and/or isoxazoline diester in enantiomerically-pure or enantiomerically-enriched form.

The specification including the figures, describe certain embodiments of the invention. A person of ordinary skill should realize, however, from the description therein that the invention is capable of modifications in various aspects, all without departing from the spirit and scope of the invention. Accordingly, the specification and figures are to be regarded as illustrative in nature and not restrictive.

DESCRIPTION

Figure 1:
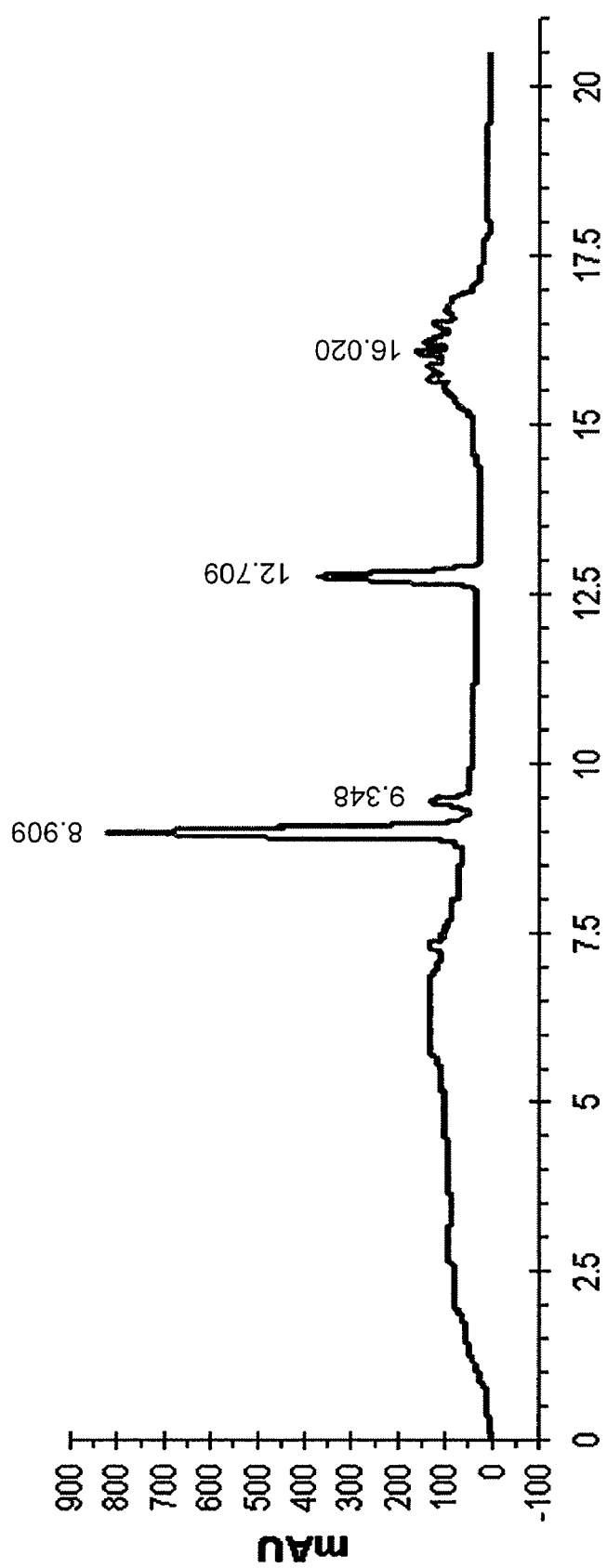
FIG. 1 is an LC-chromatogram of the reaction of isoxazoline diester (Formula II, $R^1$ and $R^2$ are ethyl) with carboxyesterase NP.

This disclosure provides methods for stereoselectively hydrolyzing a stereoisomeric mixture of isoxazoline diester. This disclosure also provides enzymes capable of preferentially hydrolyzing one isoxazline diester isomer over another isoxazoline diester. This disclosure also provides methods of identifying enzymes capable of stereoselectively hydrolyzing isomeric mixtures of isoxazoline diesters.

This disclosure provides methods for producing mixtures of (R,R) and (R,S) monatin as well as mixtures of (S,S) and (S,R) monatin. The disclosure also provides methods for producing single isomers of monatin. In some embodiments, the method comprises using an enzyme to preferentially hydrolyze one isoxazoline diester isomer over another into a monoester, separating the monoester from the diester, converting the isoxazoline monoester into a mixture of monatin diastereomers and resolving those diastereomers using physical means known in the art, and converting the isoxazoline diester into a mixture of monatin diastereomers and resolving those diastereomers using physical means known in the art.

Each reference herein to a molecule containing chiral centers, refers to all stereoisomeric forms of the molecule, unless otherwise specified. Although each stereoisomer is a distinct compound, in practice a mixture of stereoisomers is often referred to as "a compound", such as e.g., "the compound (±) isoxazoline diethylester" or "isoxazoline diethylester". Similarly, each structural depiction of a molecule herein containing chiral centers represents all stereoisomeric forms of the molecule, unless otherwise specified, for example through use of wedge diagrams to show three-dimensional conformation.

Also, unless otherwise specified or unless otherwise clear from the context, references to "R,R monatin" or "S,S monatin" mean the single stereoisomer of monatin or a mixture enriched in the specified stereoisomer. "Enriched" means that the mixture includes a higher ratio of designated stereoisomer to non-designated stereoisomer as compared to the original mixture from which it was obtained.

A single stereoisomer can be differentiated from a stereoisomerically-enriched mixture of stereoisomers by referring to the former as a "single stereoisomer" or "single isomer" or "single enantiomer," as appropriate. Thus, for example, unless otherwise specified or unless otherwise clear from the context, "(S,S) monatin" indicates the single stereoisomer of monatin with S configuration at each stereogenic center, or a mixture enriched in which (S,S) monatin.

Additionally, each compound formula designated with a Roman numeral will follow a convention herein of meaning a single stereoisomer or a mixture enriched in that stereoisomer when followed by a lower case letter. For example, reference to "a compound" of Formula II:

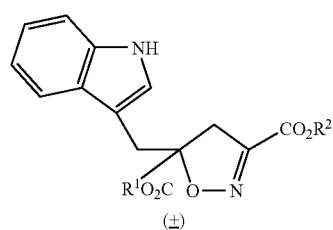

II (±)

refers to an isomeric mixture of the compound shown. (The use or "(±)" is included for clarity to designate that the indicated formula includes a mixture of isomeric forms.) Similarly, reference to "a compound" of Formula IIa:

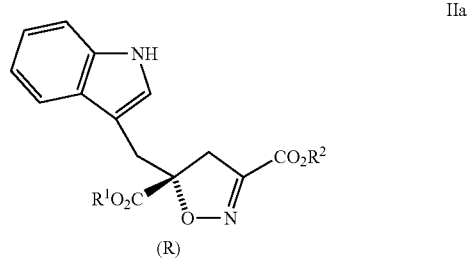

IIa (R)

refers to both the single enantiomer shown and to a mixture enriched in that enantiomer, unless otherwise specified or unless otherwise clear from the context. (The use of "(R)" is included for to designate that the indicated formula represents the R isomer or a mixture enriched in the R isomer.) Typically, for the compounds described herein, the letter "a" will designate compounds having an "R" configuration, or where the compound includes two chiral centers "a" designates the "R,R" or "R,S" configurations; and, "b" will designate compounds having an "S" configuration or where two chiral centers are present, the "S,S" or "S,R" configurations.

Unless otherwise specified, the terms "include," "includes," "including" and the like are intended to be open-ended. Thus, for example, "include" means "include but are not limited to."

Except as otherwise noted, the articles "a," "an," and "the" mean "one or more."

As used herein, the term "about" encompasses the range of experimental error that occurs in any measurement. Unless otherwise stated, all measurements are presumed to have the word "about" in front of them even if the word "about" is not expressly used.

The term "alkyl" as employed herein by itself or as part of another group refers to both straight and branched chain saturated radicals of up to 10 carbons, unless the chain length is otherwise limited, such as methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl, nonyl, decyl and the like.

An overall process according to an embodiment of the invention is illustrated in Schemes 1a and 1b, below.

Scheme 1a

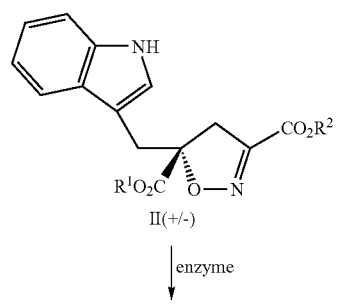

II(+/-)

↓ enzyme

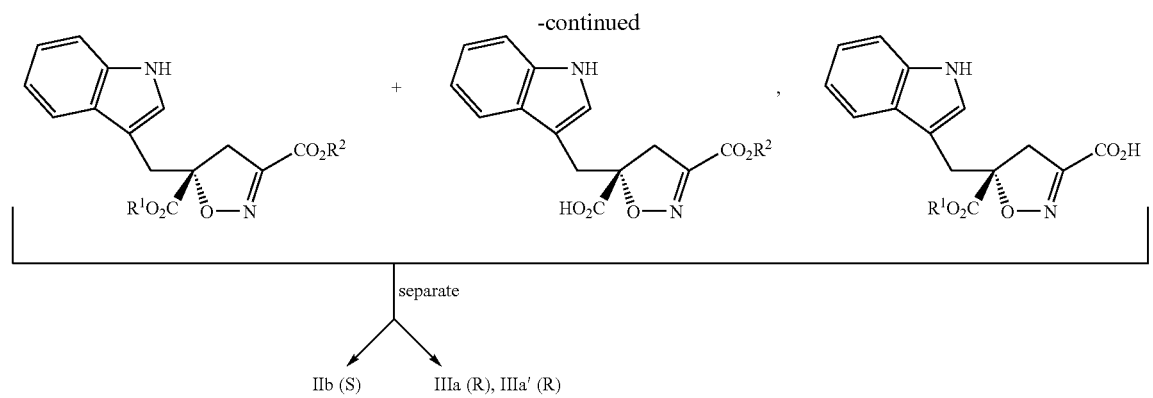

IIb (S)    IIIa (R), IIIa' (R)

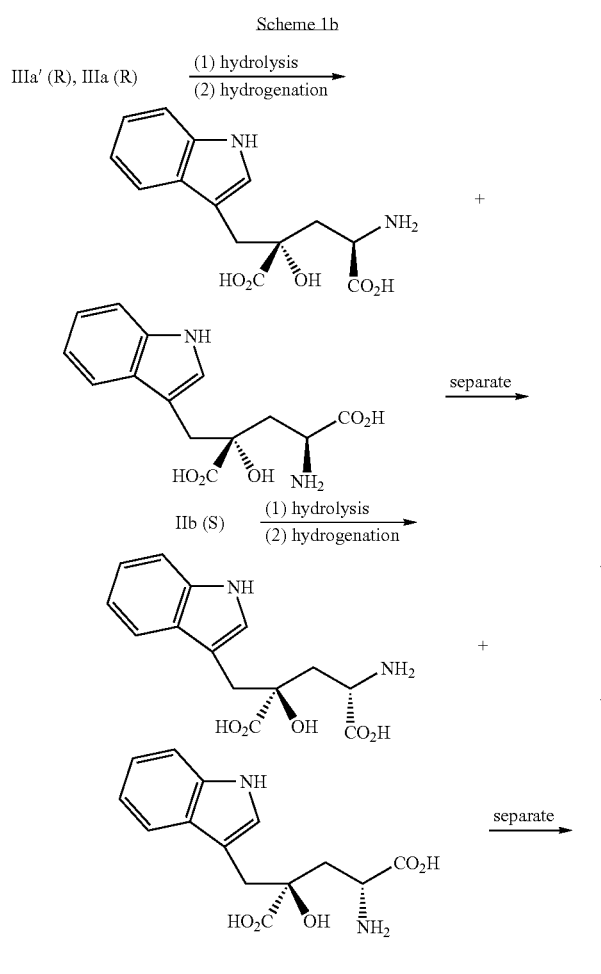

As Scheme 1a illustrates, the selected enzyme stereoselectively hydrolyzes one isomer over another isomer, and in the embodiment illustrated the R-isomer is preferentially hydrolyzed over the S-isomer. Although Scheme 1a indicates that the R-isomer may undergo hydrolysis at both esters, it is believed that the selected enzyme will largely cleave only one of the esters. For example, it is believed that the carboxylesterase NP (DSM) largely cleaves the —CO$_2$R$^2$ ester. In particular, an experiment carried out on a mixed methyl/ester diester showed that while the carboxylesterase enzyme was able to cleave both esters, greater than about 75% of the product was the compound of Formula IIIa'. There was approximately 10% of the other regioisomer present in the reaction.

In some embodiments, the present invention is directed to a process comprising: hydrolyzing a compound of Formula II:

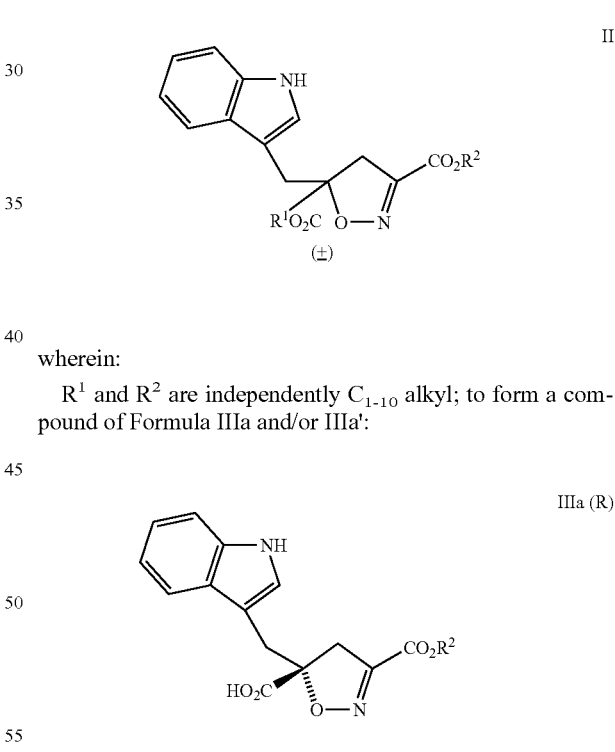

wherein:

R$^1$ and R$^2$ are independently C$_{1-10}$ alkyl; to form a compound of Formula IIIa and/or IIIa':

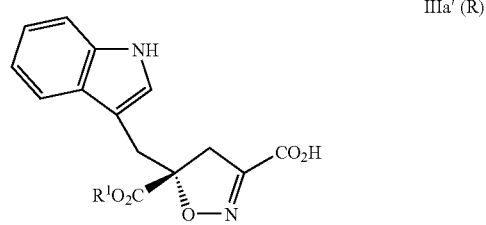

and a compound of Formula IIb:

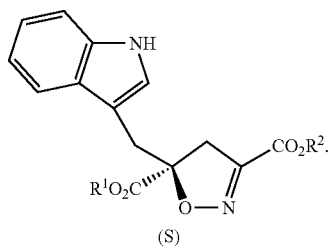

The compounds of Formula IIIa/IIIa' and IIb are useful in the production of (R,R)-monatin and (S,S)-monatin, respectively.

Useful values of $R^1$ and $R^2$ include $C_{1-10}$ alkyl, particularly $C_{1-6}$ alkyl, more particularly $C_{1-4}$ alkyl. Examples of useful values of $R^1$ and $R^2$ include methyl, ethyl, propyl, isopropyl and butyl, especially methyl and ethyl. In some embodiments, $R^1$ and $R^2$ are both ethyl.

The compound of Formula II can be synthesized by methods known in the art. For example, synthesis of the compound of Formula II in which $R^1$ is methyl and $R^2$ is ethyl is described in C. W. Holzapfel, *Synth. Comm.* 24:3197-3211 (1994). See also U.S. Pat. No. 5,128,482.

It will be apparent to one of ordinary skill in the art that the compound of Formula IIb is "formed" from the compound of Formula II by depletion of the other enantiomer. That is, if the compound of Formula II is recognized as the mixture of the compound of Formula IIa and the compound of Formula IIb (for example, a racemic mixture of the compound of Formula IIa and the compound of Formula IIb), then the preferential conversion of IIa to IIIa results in enrichment of the starting racemate in the unhydrolyzed enantiomer. Thus, the starting racemate II becomes a "compound of Formula IIb" using the previously described nomenclature.

One of ordinary skill in the art will also appreciate that few, if any, stereospecific reactions perfectly discriminate between stereoisomers. Thus, hydrolysis of a compound of Formula II may result in the formation of a compound of Formula IIIb:

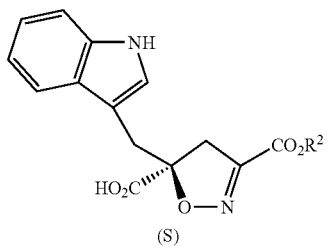

via undesired hydrolysis of IIb. Such a result is contemplated by the present invention, provided that the amount of the single enantiomer of Formula IIIb formed is less than the amount of the target single enantiomer formed (i.e., Formula IIIa and/or IIIa').

Hydrolysis of the compound of Formula II may be accomplished enzymatically or non-enzymatically. In an embodiment, enzymatic hydrolysis may be accomplished using, the carboxy esterase, Carboxyesterase NP. The enzyme activity Carboxylesterase NP was first discovered in *Bacillus thai* 1-8, which was deposited under the accession number CBS 679.85 (Yuki, S., 1967, Jpn. J. Genet. 42 p 251). The gene for Carboxylesterase NP was subsequently cloned into *Bacillus subtilis* 1-85/pNAPT-7, which was deposited under the accession number CBS 673.86 (W J Quax and C. P. Broekhuizen 1994. *Development of a new Bacillus carboxyl esterase for use in the resolution of chiral drugs*. Journal Applied Microbiology and Biotechnology 41: 425-431). This was the organism used in the present studies. The gene was also cloned and deposited as *Bacillus subtilis* 1A-40/pNAPT-8 (CBS 674.86), and *Bacillus subtilis* 1A-40/pNAPT-7 (CBS 675.86). The gene sequence for Carboxylesterase NP has been published (Melloney J. Dröge, Rein Bos and Wim J. Quax (2001). Paralogous gene analysis reveals a highly enantioselective 1,2-O-isopropylideneglycerol caprylate esterase of *Bacillus subtilis*. Eur. J. Biochem. 268: 3332-3338).

The products of the enzymatic reaction, for example, compounds of Formula IIIa and Formula IIb, can be separated using chromatographic techniques. One embodiment of the method of the invention is exemplified in FIG. 1. As shown on FIG. 1, isoxazoline diester (Formula II, $R^1$ and $R^2$ are ethyl) was enzymatically reacted with carboxyesterase NP and the products were separated and analyzed by LC-MS (liquid chromatography-mass spectrometry) chromatography (here, exemplified using a Waters Platform LC-MS system).

Further or alternatively, taking advantage of the different reactivities of carboxylic acids and esters (see March and Larock, supra) one of the compounds of Formula IIIa or Formula IIb may be transformed into a different compound prior to separation from the other. For example, borane reduces carboxylic acids much more readily than it does esters (see, e.g., March at pages 1544-46). Thus, the mixture can be subjected to reducing conditions using borane that will selectively reduce the compound of Formula IIIa to its corresponding alcohol. This alcohol can then be separated from the compound of Formula IIb by standard techniques, such as chromatography. The present invention contemplates any such separation of the compound of Formula IIIa, or a compound derived from it, from the compound of Formula IIb, or a compound derived from it, following the selective hydrolysis described above, as "separating the compound of Formula IIIa from the compound of Formula IIb" as a means to obtaining enantiomerically pure or enantiomerically enriched (R,R)- or (S,S)-monatin.

In some embodiments, the present invention further comprises converting the compound of Formula IIIa into a compound of Formula Ia:

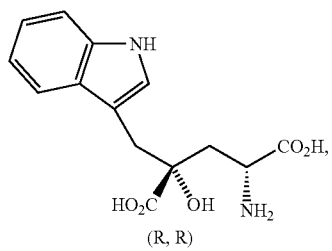

i.e., into (R,R)-monatin.

In some embodiments, conversion of the compound of Formula IIIa into a compound of Formula Ia may be accomplished by (a) hydrolyzing the compound of Formula IIIa to form a compound of Formula IVa:

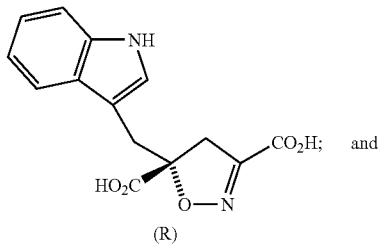

(b) hydrogenating the compound of Formula IVa.

Useful reagents for hydrolysis are well known to those of ordinary skill in the art and are described in, e.g., M. B. Smith and J. March, *March's Advanced Organic Chemistry*, 5th ed., New York: John Wiley & Sons, Inc., 2001 ("March"), particularly at pages 469-74; and R. C. Larock, *Comprehensive Organic Transformations*, 2nd ed., New York: John Wiley & Sons, Inc., 1999 ("Larock"), particularly at pages 1959-68. Examples of useful reagents for hydrolysis include Group IA and IIA alkoxides such as LiOH, NaOH, KOH and Ba(OH)$_2$. Other useful reagents include Sm/I$_2$/MeOH and MgI$_2$. Methyl esters may also be cleaved with, e.g., (Na$_2$CO$_3$ or K$_2$CO$_3$)/MeOH/H$_2$O, NaO$_2$/DMSO, KSCN/DMF, EtSH/(AlCl$_3$ or AlBr$_3$), Me$_2$S/(AlCl$_3$ or AlBr$_3$), (Li or Na)SeCH$_3$/DMF, NaCN/HMPA, (LiI or LiBr)/DMF, LiI/(NaOAc or NaCN)/DMF, BCl$_3$, AlI$_3$ or MeSiCl$_3$. In some embodiments, hydrolysis is carried out using KOH in an alcoholic solvent such as MeOH or EtOH.

In addition, hydrolysis of the compound of Formula IIIa into a compound of Formula IVa can be accomplished using a hydrolase, and especially a carboxyesterase, that is capable of accepting a compound of the Formula IIIa as a product and of producing a compound of Formula IVa.

Useful conditions for hydrogenation are well known to those of ordinary skill in the art and are described in, e.g., March and Larock, supra. In some embodiments, hydrogenation is carried out using H$_2$ and a sponge nickel catalyst.

If the hydrogenation of the compound of Formula IVa is not done stereoselectively, it will form a mixture of a compound of Formula Ia and a compound of Formula Ic:

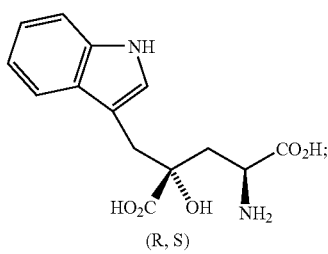

Figure 2:
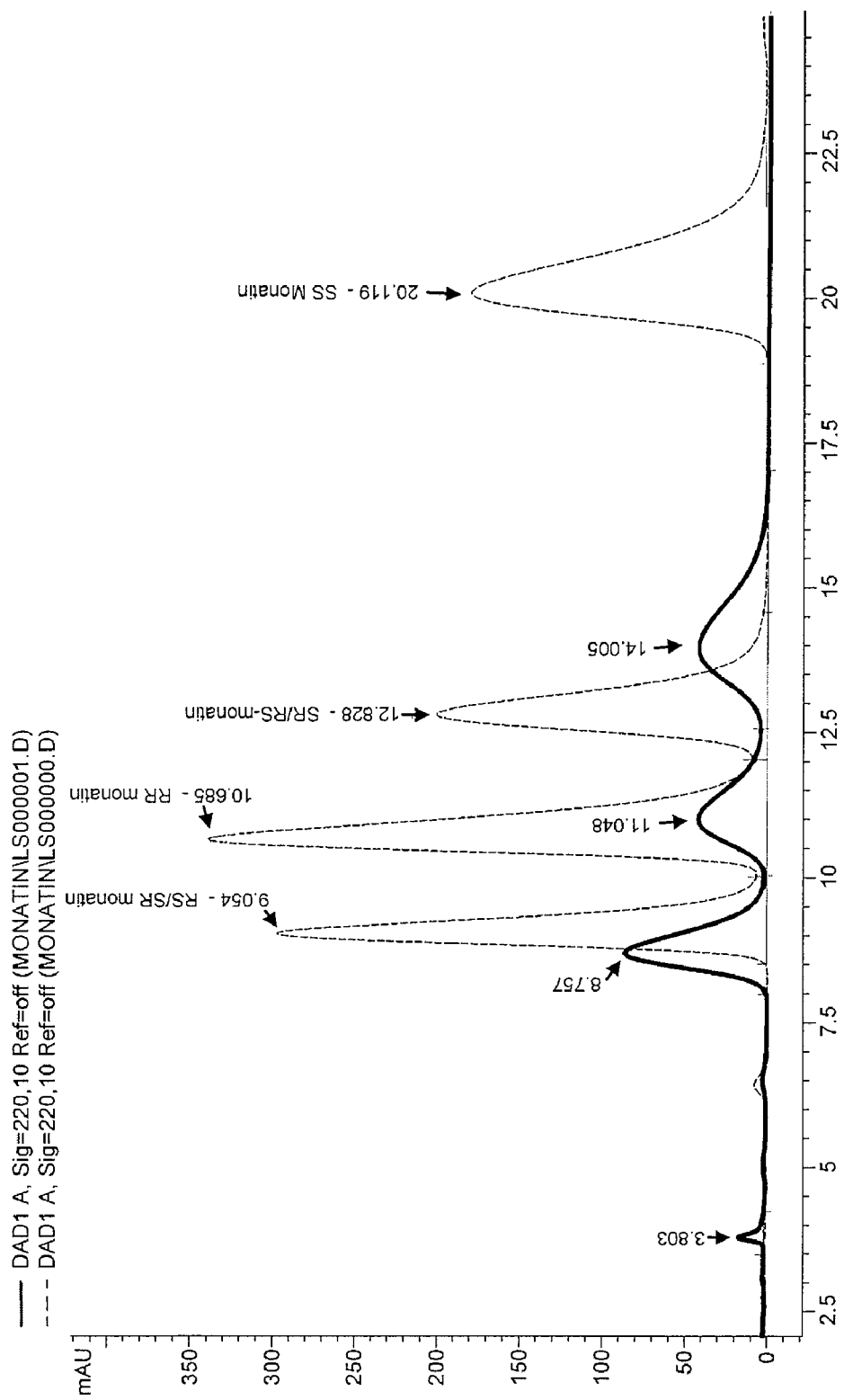
FIG. 2 is a chiral HPLC chromatogram of the carboxy esterase NP-catalyzed reaction of isoxazoline diester (Formula II, $R^1$ and $R^2$ are ethyl) giving (R,R)- and (R,S)-monatin after hydrogenation.

See, for example, FIG. 2, showing a chiral HPLC chromatogram of the carboxyesterase NP-catalyzed reaction of isoxazoline diester (Formula II, R$^1$ and R$^2$ are ethyl) giving (R,R)- and (R,S)-monatin after hydrogenation.

The compounds of Formula Ia and Formula Ic can then separated from each other, e.g., by selective crystallization. These compounds are related as diastereomers, and the separation of diastereomers is well-known and considered routine in the art. See, e.g., D. Kozma (ed.), *CRC Handbook of Optical Resolutions via Diastereomeric Salt Formation*, CRC Press: Boca Raton (2002).

In some embodiments, the present invention further comprises converting the compound of Formula IIb into a compound of Formula Ib:

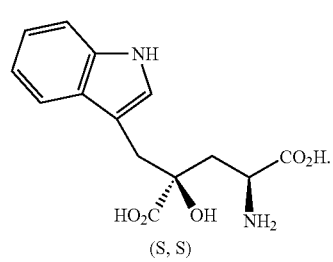

In some embodiments, conversion of the compound of Formula IIb into a compound of Formula Ib may be accomplished by (a) hydrolyzing the compound of Formula IIb to form a compound of Formula IVb:

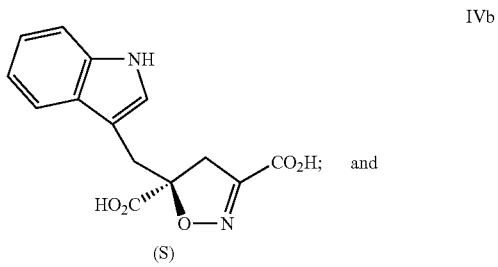

(b) hydrogenating the compound of Formula IVb.

If the hydrogenation of the compound of Formula IVb is not done stereoselectively, it will form a mixture of a compound of Formula Ib and a compound of Formula Id:

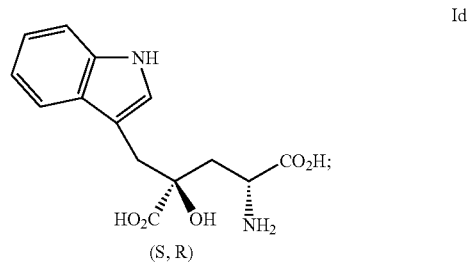

The compounds of Formula Ib and Formula Id can then be separated from each other. These compounds are related as diastereomers, and, as discussed above, the separation of diastereomers is well-known and considered routine in the art.

Certain processes of the invention are illustrated in the following examples. While multiple embodiments are disclosed herein, still other embodiments of the present invention may become apparent to those skilled in the art from review of the entirety of this specification. As should be realized from the description herein, the invention is capable of modifications in various aspects, all without departing from the spirit and scope of the present invention. Accordingly, the drawing and entirety of the description are to be regarded as illustrative in nature and not in a limiting sense.

EXAMPLES

Example 1

Screening of Hydrolytic Enzymes for Isoxazoline Diester

The screening is done in 0.1 M sodium phosphate buffer pH 7. 1% Triton X-100 is added to the buffer and then isoxazoline diester is added slowly at 37° C. until saturation is reached.

Aliquots of 1.5 ml of the above solution are placed in Eppendorff tubes and different hydrolytic enzymes are added to the tubes. A microspatula tip of the powdered enzymes is used or 100 µl of the liquid enzymes. The reactions are incubated for 20 hours on a vibrating shaker at an appropriate temperature, generally, room temperature.

Following the incubations, the reaction mixtures are centrifuged at 10,000 rpm for 2 minutes to remove any insoluble material. The samples are then analysed on HPLC. A Phenomenex Luna C18 column is used as a linear gradient consisting of eluent A: 0.1% $H_3PO_4$ in TEA pH 3.5 and eluent B: 100% acetonitrile.

Example 2

Evaluation of Carboxylesterase NP (DSM) Activity for Isoxazoline Diester

Only Carboxylesterase NP, was tested for activity according to the protocol in Example 1. The HPLC yielded a single product peak, and corresponding to enantiopure R-monatin according to chiral-HPLC and LC-MS following hydrogenation and workup.

Example 3

Synthesis of Monatin

Carboxylesterase NP was re-tested on 10 ml scale in order to do further analytical work.

10 ml of a 0.1 M sodium phosphate buffer containing 1% Triton X-100 was placed in a test tube. 50 mg of substrate was added and either 50 mg of the dry enzyme or 1 ml of the liquid enzyme. The tube was sealed and the reaction shaken at 180 rpm for 20 hours at 40° C. (to prevent microbial growth). The unreacted substrate was removed by centrifugation at 3000 rpm for 3 minutes and any excess substrate removed by extraction with an equal volume of ethyl acetate. The aqueous phase was the hydolysed with KOH and then hydrogenated to yield monatin.

The reaction resulted in R'R' monatin as well as R'S' monatin in approximately equal amounts as determined by achiral and chiral analysis as well as LS-MS. FIG. 2 is a chiral HPLC chromatogram of the carboxy esterase NP-catalyzed reaction of isoxazoline diester (Formula II, $R^1$ and $R^2$ are ethyl) giving (R,R)- and (R,S)-monatin after hydrogenation.

Example 4

Enzymatic Hydrolysis of Isoxazoline Diester with Carboxylesterase NP

The reaction was done in 0.1 M phosphate buffer containing 1% Triton X-100 at 37° C. and pH 7. The substrate isoxazoline diester was added to 200 mL of the buffer, and the mixture was stirred until a saturated solution was reached. 200 mL of the liquid enzymes Carboxylesterase NP (DSM) was added to 2 mL of reaction mixture. The reaction was agitated at 40° C. for 20 hours at 230 rpm. At the end of the reaction, the reaction mixture was transferred to an Eppendorf tube and centrifuged to remove any undissolved material. The supernatant was analyzed on a Waters Platform LC-MS system. The reaction mixture was extracted with ethyl acetate to remove unreacted substrate, leaving the hydrolyzed product in the aqueous reaction mixture. The chromatographic separation, the output is shown in FIG. 1, was on a Waters Alliance 2695 HPLC system and a Phenomenex Gemini C18 column (250 mm×2.1 mm (5 µm)). The starting eluent was 95% water containing 10 mM ammonium acetate (pH 4.5 with acetic acid) and 5% acetonitrile. These conditions were maintained for 5 minutes followed by a linear gradient to 100% acetonitrile at 15 minutes, and then maintained at 100% acetonitrile for 2 minutes. The column was then returned to initial conditions and allowed to stabilize for 7 minutes. The total run time was 30 minutes. The flow rate was 0.2 mL/min and the column temperature was kept stable at 40° C. The mass spectrometer was operated in electrospray mode, utilising +/− voltage switching. The analysis conditions can be summarised as follows:

Capillary voltage 2.5 kV; Cone voltage 25 V; Extractor lens voltage 1 V; RF lens voltage 0.5 V; Source block temperature 120° C.; desolvation temperature 450° C.; Mass range scanned 100-400 Daltons (0.5 seconds cycle time). Nitrogen was used as nebulization and desolvation gas at a flow rate of 75 and 575 l/hr respectively. A Waters 2996 Photo Diode Array (PDA) detector was used to optimize the chromatographic separation and was used in scan mode covering the 200-600 nm wavelength range.

Example 5

Chemical Hydrolysis and Hydrogenation

The reaction was carried out in a 20 mL pressure reactor. The reaction mixture as produced in Example 2 (10 mL volume containing 25 mg of monoester) was treated with ethanol (1.5 mL) and the pH was adjusted to 12 with potassium hydroxide (200 mg). The resulting mixture was stirred at room temperature for 30 minutes, after which analysis by HPLC showed complete hydrolysis to the diacid. To this mixture was added a sponge nickel catalyst (A-7063, 50 mg) as a wet paste containing about 50% water. The reactor was sealed, evacuated and purged with hydrogen gas three times, after finally pressurizing the vessel to 5 bar with hydrogen. The reaction was continued for 60 minutes under these conditions with stirring, and monitored by HPLC.

Having now filly described this invention, it will be understood by those of ordinary skill in the art that the same can be performed within a wide and equivalent range of conditions, formulations and other parameters without affecting the scope of the invention or any embodiment thereof. All patents and publications cited herein are filly incorporated by reference herein in their entireties.

What is claimed is:
1. A process comprising:
stereoselectively hydrolyzing a compound of formula II using carboxylesterase NP enzyme by contacting the compound of formula II with carboxylesterase NP enzyme:

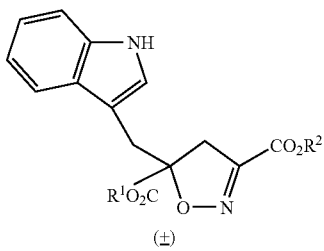

II(±)

wherein:

$R^1$ and $R^2$ are independently $C_{1-10}$ alkyl;

to form at least one of a compound of formula IIIa:

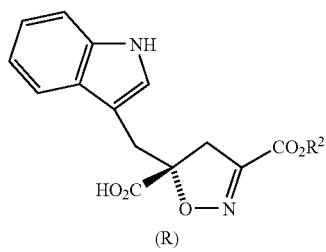

IIIa (R)

or a compound of formula IIIa'

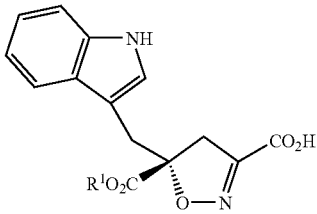

and a compound of formula IIb:

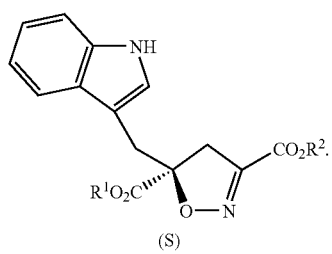

2. The process of claim 1, wherein $R^1$ and $R^2$ are both ethyl.

3. The process of claim 1, further comprising converting the compound of formula IIIa or IIIa' or both into a compound of formula Ia:

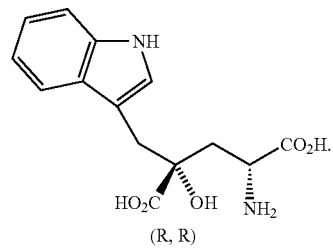

4. The process of claim 3, wherein said converting comprises:

(a) hydrolyzing the compound of formula IIIa or IIIa' to form a compound of formula IVa:

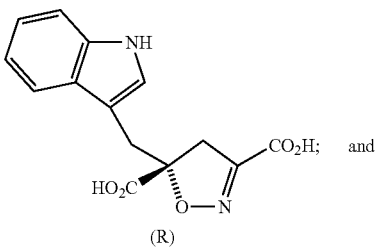

IVa (R); and (b) and hydrogenating the compound of formula IVa.

5. The process of claim 4, wherein said hydrogenating forms a mixture of a compound of formula Ia and a compound of formula Ic:

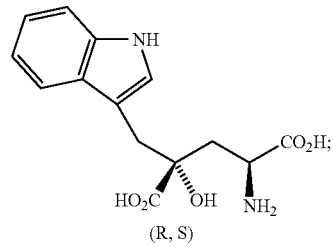

Ic (R, S);

and the process, further comprises separating the compound of formula Ia from the compound of formula Ic.

6. The process of claim 1, further comprising converting the compound of formula IIb into a compound of formula Ib:

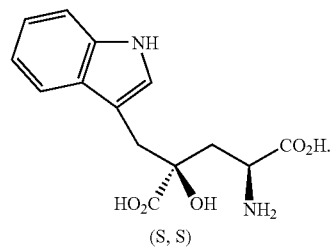

Ib (S, S).

7. The process of claim 6, wherein said converting comprises:

(a) hydrolyzing the compound of formula IIb to form a compound of fomula IVb:

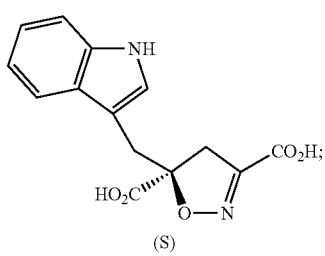

IVb (S);

(b) and hydrogenating the compound of formula IVb.

8. The process of claim 7, wherein said hydrogenating forms a mixture of a compound of formula Ib and a compound of formula Id:

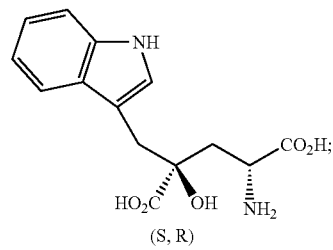

Id (S, R);

and the process further comprises separating the compound of formula Ib from the compound of formula Id.

9. The process of claim 5, further comprising:

(a) incorporating the compound of formula Ia into a food composition.

10. A process comprising:

stereoselectively hydrolyzing a compound of formula II by contacting the carboxylesterase NP enzyme from *Bacillus subtilis*:

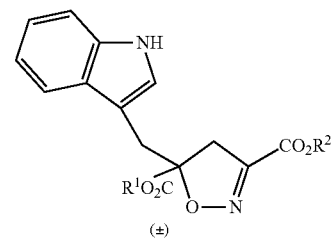

II(±)

wherein:

$R^1$ and $R^2$ are independently $C_{1-10}$ alkyl;

to form at least one of a compound of formula IIIa:

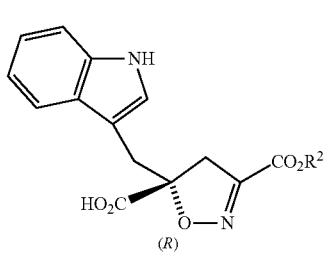

IIIa (R)

or a compound of formula IIIa'

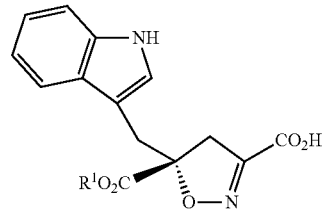

and a compound of formula IIb:

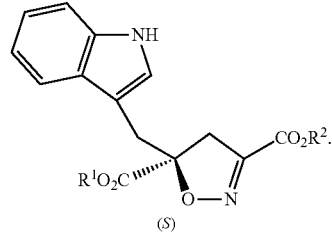

IIb (S).

11. The process of claim 10, wherein $R^1$ and $R^2$ are both ethyl.

12. The process of claim 10, further comprising converting the compound of formula IIIa or IIIa' or both into a compound of formula Ia:

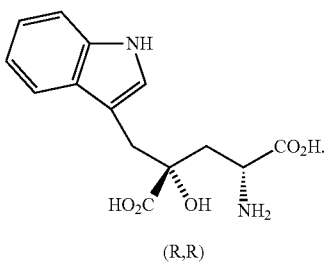

(R,R)

13. The process of claim 12, wherein said converting comprises:
(a) hydrolyzing the compound of formula IIIa or IIIa' to form a compound of formula IVa:

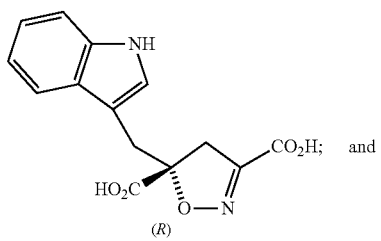

IVa (R); and
(b) and hydrogenating the compound of formula IVa.

14. The process of claim 13, wherein said hydrogenating forms a mixture of a compound of formula Ia and a compound of formula Ic:

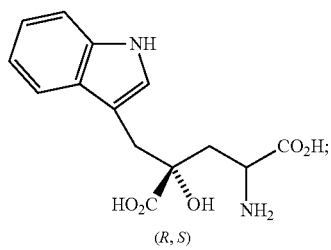

Ic (R, S);

and the process, further comprises separating the compound of formula Ia from the compound of formula Ic.

15. The process of claim 14, further comprising:
(a) incorporating the compound of formula Ia into a food composition.

* * * * *